United States Patent [19]
Berg

[11] Patent Number: 6,048,362
[45] Date of Patent: Apr. 11, 2000

[54] FLUOROSCOPICALLY-VISIBLE FLEXIBLE GRAFT STRUCTURES

[75] Inventor: Todd Allen Berg, Lino Lakes, Minn.

[73] Assignee: St. Jude Medical Cardiovascular Group, Inc., Minneapolis, Minn.

[21] Appl. No.: 09/005,533

[22] Filed: Jan. 12, 1998

[51] Int. Cl.⁷ .................................................. A61F 2/00
[52] U.S. Cl. .................................................. 623/1.34
[58] Field of Search ................... 623/1, 12, 1.34

[56] References Cited

U.S. PATENT DOCUMENTS

| | | | |
|---|---|---|---|
| 4,214,587 | 7/1980 | Sakura, Jr. | 128/334 |
| 4,459,252 | 7/1984 | MacGregor | 264/46.9 |
| 4,487,567 | 12/1984 | Possis et al. | 425/403 |
| 4,503,569 | 3/1985 | Dotter | 3/1.4 |
| 4,546,499 | 10/1985 | Possis et al. | 623/1 |
| 4,562,597 | 1/1986 | Possis et al. | 623/1 |
| 4,592,754 | 6/1986 | Gupte et al. | 623/1 |
| 4,601,718 | 7/1986 | Possis et al. | 623/1 |
| 4,605,406 | 8/1986 | Cahalan et al. | 623/1 |
| 4,617,932 | 10/1986 | Kornberg | 128/334 |
| 4,629,458 | 12/1986 | Pinchuk | 623/1 |
| 4,632,842 | 12/1986 | Karwoski et al. | 427/2 |
| 4,657,544 | 4/1987 | Pinchuk | 623/1 |
| 4,665,906 | 5/1987 | Jervis | 128/92 |
| 4,705,517 | 11/1987 | DiPisa, Jr. | 623/12 |
| 4,718,907 | 1/1988 | Karwoski et al. | 623/12 |
| 4,733,665 | 3/1988 | Palmaz | 128/343 |
| 4,738,740 | 4/1988 | Pinchuk et al. | 156/167 |
| 4,743,252 | 5/1988 | Martin, Jr. et al. | 623/1 |
| 4,759,757 | 7/1988 | Pinchuk | 623/1 |
| 4,776,337 | 10/1988 | Palmaz | 623/1 |
| 4,787,899 | 11/1988 | Lazarus | 623/1 |
| 4,798,606 | 1/1989 | Pinchuk | 623/1 |
| 4,892,539 | 1/1990 | Koch | 623/1 |
| 4,909,979 | 3/1990 | Possis et al. | 264/571 |
| 4,955,899 | 9/1990 | Della Corna et al. | 623/901 |
| 4,994,071 | 2/1991 | MacGregor | 623/12 |
| 5,037,377 | 8/1991 | Alonso | 600/36 |
| 5,061,275 | 10/1991 | Wallsten et al. | 623/1 |
| 5,084,065 | 1/1992 | Weldon et al. | 623/1 |
| 5,100,422 | 3/1992 | Berguer et al. | 606/151 |
| 5,104,399 | 4/1992 | Lazarus | 623/1 |

(List continued on next page.)

FOREIGN PATENT DOCUMENTS

| | | | |
|---|---|---|---|
| 670239 | 7/1996 | Australia | A61F 2/06 |
| 0 539 237 A1 | 4/1993 | European Pat. Off. | A61F 2/06 |
| 0 637 454 A1 | 2/1995 | European Pat. Off. | A61M 25/10 |
| 0 680 734 A2 | 11/1995 | European Pat. Off. | A61F 2/06 |
| 0 684 022 A2 | 11/1995 | European Pat. Off. | A61F 2/06 |
| WO 94/06372 | 3/1994 | WIPO | A61F 2/04 |
| WO 96/01591 | 1/1996 | WIPO | A61B 17/22 |
| WO 96/01599 | 1/1996 | WIPO | A61F 2/06 |
| WO 96/18361 | 6/1996 | WIPO | A61F 2/06 |

*Primary Examiner*—Michael J. Milano
*Attorney, Agent, or Firm*—Fish & Neave; Robert R. Jackson; G. Victor Treyz

[57] ABSTRACT

A fluoroscopically-visible graft structure is provided. The graft structure may be formed from a tubular metal wire mesh coated with an elastomeric material. The graft structure is flexible and distensible like natural body organ tubing and is suitable for repairing or replacing body organ tubing such as vascular tubing (e.g., arteries and veins). A radiopaque filler compound may be provided throughout a substantial portion of the graft structure or throughout the entire graft structure, so that a physician can determine the size and location of the graft structure during implantation of the graft structure in the body of a patient. The radiopacity of the graft structure also allows the physician to monitor status of the graft structure after installation. The radiopacity of the graft structure is preferably sufficient to allow the graft structure to be clearly viewable on a fluoroscope, but is not so great that the radiopacity of the graft obscures radiopaque dyes introduced into the patient and passed through the graft.

16 Claims, 4 Drawing Sheets

U.S. PATENT DOCUMENTS

| | | | |
|---|---|---|---|
| 5,104,400 | 4/1992 | Berguer et al. | 264/132 |
| 5,116,360 | 5/1992 | Pinchuk et al. | 623/1 |
| 5,122,154 | 6/1992 | Rhodes | 606/198 |
| 5,135,467 | 8/1992 | Citron | 600/16 |
| 5,152,782 | 10/1992 | Kowligi et al. | 623/1 |
| 5,163,951 | 11/1992 | Pinchuk et al. | 623/1 |
| 5,211,658 | 5/1993 | Clouse | 623/1 |
| 5,211,683 | 5/1993 | Maginot | 128/898 |
| 5,246,451 | 9/1993 | Trescony et al. | 623/1 |
| 5,246,452 | 9/1993 | Sinnott | 623/1 |
| 5,275,622 | 1/1994 | Lazarus et al. | 623/1 |
| 5,282,847 | 2/1994 | Trescony et al. | 623/1 |
| 5,304,220 | 4/1994 | Maginot | 623/1 |
| 5,306,240 | 4/1994 | Berry | 604/51 |
| 5,316,023 | 5/1994 | Palmaz et al. | 128/898 |
| 5,360,443 | 11/1994 | Barone et al. | 623/1 |
| 5,366,504 | 11/1994 | Andersen et al. | 623/11 |
| 5,387,235 | 2/1995 | Chuter | 623/1 |
| 5,395,349 | 3/1995 | Quiachon et al. | 604/248 |
| 5,397,345 | 3/1995 | Lazarus | 623/1 |
| 5,413,598 | 5/1995 | Moreland | 623/1 |
| 5,425,765 | 6/1995 | Tiefenbrun et al. | 623/12 |
| 5,429,144 | 7/1995 | Wilk | 128/898 |
| 5,443,497 | 8/1995 | Venbrux | 623/1 |
| 5,443,499 | 8/1995 | Schmitt | 623/1 |
| 5,456,712 | 10/1995 | Maginot | 623/1 |
| 5,489,295 | 2/1996 | Piplani et al. | 623/1 |
| 5,496,364 | 3/1996 | Schmitt | 623/1 |
| 5,496,365 | 3/1996 | Sgro | 623/1 |
| 5,507,769 | 4/1996 | Marin et al. | 606/198 |
| 5,509,931 | 4/1996 | Schmitt | 623/1 |
| 5,522,880 | 6/1996 | Barone et al. | 623/1 |
| 5,562,725 | 10/1996 | Schmitt et al. | 623/1 |
| 5,584,875 | 12/1996 | Duhamel et al. | 623/1 |
| 5,584,876 | 12/1996 | Bruchman et al. | 623/1 |
| 5,607,463 | 3/1997 | Schwartz et al. | 623/1 |
| 5,607,464 | 3/1997 | Trescony et al. | 623/1 |
| 5,609,624 | 3/1997 | Kalis | 623/1 |
| 5,628,782 | 5/1997 | Myers et al. | 623/1 |
| 5,628,786 | 5/1997 | Banas et al. | 623/1 |
| 5,628,788 | 5/1997 | Pinchuk et al. | 623/1 |
| 5,632,772 | 5/1997 | Alcime et al. | 623/1 |
| 5,653,747 | 8/1997 | Dereume | 623/1 |
| 5,725,572 | 3/1998 | Lam | 623/12 |

FLUOROSCOPICALLY-VISIBLE FLEXIBLE GRAFT STRUCTURES

BACKGROUND OF THE INVENTION

This invention relates to graft structures and particularly to fluoroscopically-visible flexible graft structures.

A patient's weakened or diseased body organ tubing can be replaced, repaired, or supplemented using artificial graft structures. For example, an aneurysm may be repaired by lining the patient's artery with an artificial graft structure to help contain the patient's blood within the weakened portion of the artery. Other procedures involve bypassing a section of diseased or blocked body organ tubing with artificial graft tubing.

Some artificial graft structures are flexible and distensible like natural body organ tubing. Such flexible graft structures may be formed from elastic polymer tubing or from a tube frame of a first highly elastic material (such as nitinol) covered with a second highly elastic material (such as silicone rubber). Flexible graft structures are a good replacement for a patient's natural body organ tubing. In addition, flexible graft structures are suitable for intraluminal installation, which is a relatively non-invasive technique by which grafts are introduced into the patient's body through the patient's existing body organ tubing. Such intraluminal installation techniques may be used, for example, to deliver and install grafts through a patient's vascular system as an alternative to open heart surgery. If desired, flexible graft structures can be made porous and may be provided with various coatings to improve bio-utility.

However, flexible graft structures are not inherently visible under fluoroscopic illumination. As a result, it may be difficult for a physician to view a flexible graft structure during an intraluminal insertion procedure or to determine the status of the graft structure during follow-up monitoring.

It is therefore an object of the present invention to provide fluoroscopically-visible flexible graft structures that allow the physician to view the graft structure during intraluminal installation and that allow the physician to monitor the status of the installed flexible graft structure during follow-up procedures.

SUMMARY OF THE INVENTION

These and other objects of the invention are accomplished in accordance with the principles of the present invention by providing a fluoroscopically-visible flexible graft structure. The graft structure may be used to replace, repair, or supplement a diseased or damaged portion of the patient's vascular system or other body organ tubing. The graft structure is preferably flexible and distensible like natural body organ tubing and may be provided with bio-compatible coatings or be made porous to enhance bio-compatibility.

In a preferred embodiment, the flexible graft structure is made from an elastic tubular wire mesh coated with an elastic polymer such as silicone. A radiopaque substance such as a radiopaque filler compound containing barium, bismuth, or tungsten is added to the elastic polymer to make the flexible graft structure radiopaque. The graft structure is preferably radiopaque enough to be clearly visible on a fluoroscope when inside the patient's body, but is not so radiopaque as to obscure standard radiopaque dyes when they pass through the graft structure. The radiopaque filler compound is preferably distributed fairly uniformly throughout a substantial portion (e.g. greater than about 50%) of the elastic material or throughout the entire elastic material, so that the size and shape of the graft structure may be viewed fluoroscopically during installation of the graft structure into the body of the patient.

The radiopacity of the flexible graft structure allows the physician to monitor the status of the flexible graft structure during follow-up procedures. Characteristics of the flexible graft structure that may be monitored include the compliance of the graft, the anastomosis of the graft to the patient's body organ tubing, and the presence or absence of conditions such as holes, kink failures, bursts, aneurysm, etc.

Further features of the invention, its nature and various advantages will be more apparent from the accompanying drawings and the following detailed description of the preferred embodiments.

DETAILED DESCRIPTION OF THE PREFERRED EMBODIMENTS

Figure 1:
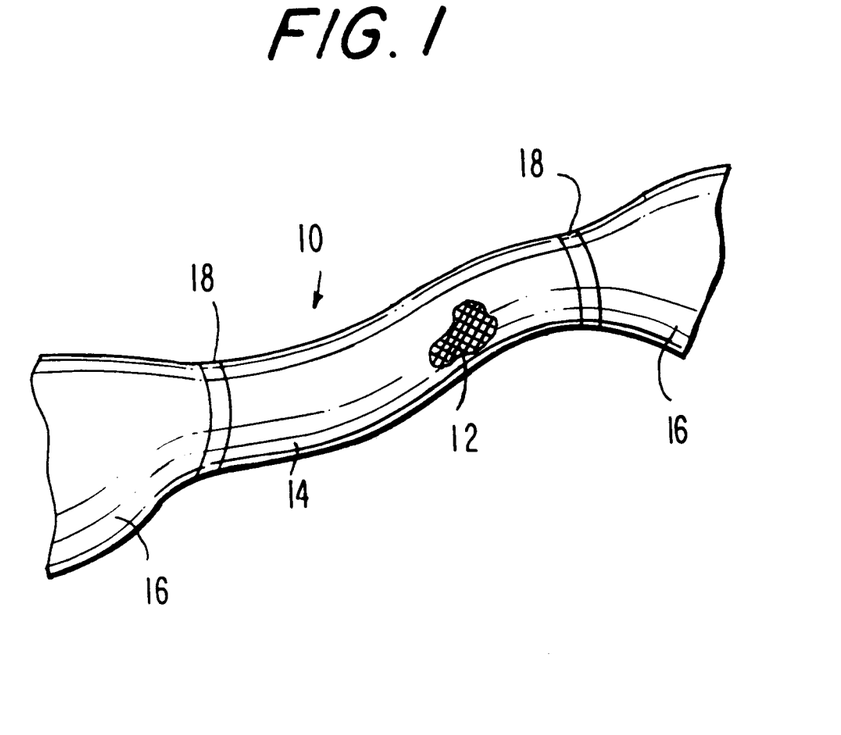
FIG. 1 is a perspective partly cut-away view of an illustrative flexible graft structure connected to a portion of a patient's body organ tubing in accordance with the present invention.

An illustrative flexible graft structure 10 in accordance with the present invention is shown in FIG. 1. Graft structure 10 may be formed from any suitable elastic tubing structure such as a polymer tube, but is preferably formed from a highly elastic tubular frame 12 with an integrally-formed highly elastic fluid-retaining coating 14. In the illustrative example of FIG. 1, graft structure 10 is connected to a patient's body organ tubing 16 with connectors 18. Connectors 18 may be formed from sutures, crimp or clamp connectors, connectors with barbs or hooks, or any other suitable connector structures. Connector structures for attaching graft structure 10 to body organ tubing 16 are described in Goldsteen et al. U.S. patent application Ser. No. 08/745,618, filed Nov. 7, 1996, which is hereby incorporated by reference herein in its entirety.

Graft structure 10 is extremely elastic, flexible, pliable, and resilient. For example, it can be stretched to a small fraction of its original diameter, after which it returns by itself to its original size and shape without damage or permanent deformation of any kind. Graft structure 10 is also preferably distensible, so that it may pulsate very much like natural circulatory system tubing in response to pressure waves in the blood flow. Graft structure 10 may also be modular in construction, may accept natural body organ tubing concentrically inside itself, may support development of an endothelial layer, and may be compatible with magnetic resonance imaging (MRI) procedures.

The preferred materials for forming frame 12 of graft structure 10 are metals, although polymeric materials may also be used. The presently most preferred material is a braid of nitinol wire. Coating 14 is preferably an elastic bio-compatible material such as silicone, which fills the apertures formed by the wires in frame 12. Other materials that may be used for coating 14 include polymeric materials such as stretchable urethane, stretchable polytetrafluoroethylene (PTFE), natural rubber, and the like.

If desired, coating 14 can be formed with microscopic pores to help improve bio-compatibility. A preferred method of providing a desired porosity is to make coating 14 from an elastic material that is mixed with particles of a material that can be removed (e.g., by vaporization) after coating 14 has been applied to frame 12. When the particles are removed, voids are left in coating 14 that give it porosity. Whether porous or not, coating 14 is preferably capable of retaining fluids. Graft structure 10 is therefore suitable for confining blood within a weakened artery and relieving pressure from the weakened artery wall.

If desired, graft structure 10 may be provided with additional coatings such as medicated coatings, hydrophilic coatings, smoothing coatings, collagen coatings, human cell seeding coatings, etc., as described in the above-mentioned Goldsteen et al. U.S. patent application. The porosity of coating 14 may help graft structure 10 to retain these coatings.

Figure 2:
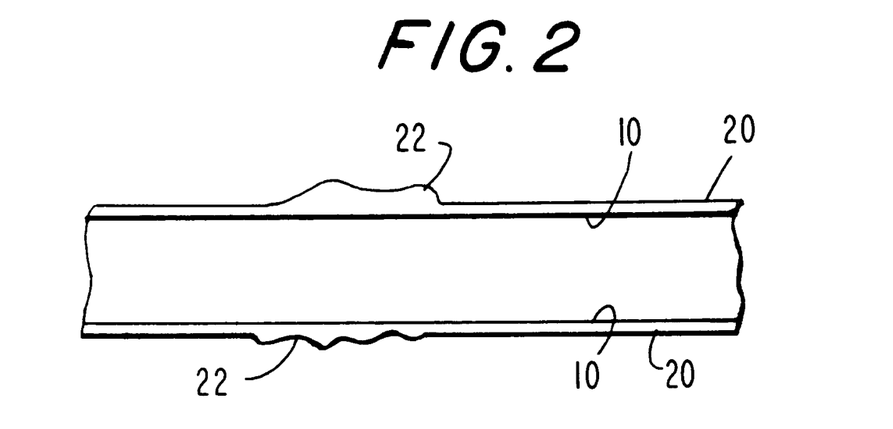
FIG. 2 is a sectional side view of an illustrative flexible graft structure used to reinforce a weakened portion of a patient's body organ tubing in accordance with the present invention.

The highly elastic nature of frame 12 and coating 14 make it possible to axially stretch and thereby radially compress graft structure 10 prior to installation in the body organ tubing of the patient. Graft structure 10 may therefore be deployed through tubes (e.g., arteries) of smaller diameter in the patient's body after which graft structure 10 automatically returns to nearly its full nominal diameter. Intraluminal installation procedures for flexible artificial graft structures are described in the above-mentioned Goldsteen et al. U.S. patent application. Using such intraluminal installation procedures, graft structure 10 may be used to replace, repair, or supplement the patient's body organ tubing. In the example of FIG. 1, graft structure 10 has been used to replace a length of natural body organ tubing. In FIG. 2, graft structure 10 has been used to line an existing artery 20 to support weakened artery wall portion 22. Although intraluminal installation is a preferred technique for implanting graft structure 10 in the patient's body, alternative installation techniques such as conventional surgery may also be used if desired.

One of the concerns of the physician during installation of structures such as graft structure 10 is whether the graft has been placed properly in the body. Proper graft placement is of particular concern during intraluminal installation, because the physician cannot view the graft site directly. Another concern of the physician is providing adequate follow-up monitoring of the implanted graft. Assessing proper graft placement and monitoring the status of the graft after implantation is difficult with flexible grafts, because the polymer coating and wire mesh frames of such grafts typically do not image well using fluoroscopic imaging devices.

Figure 3:
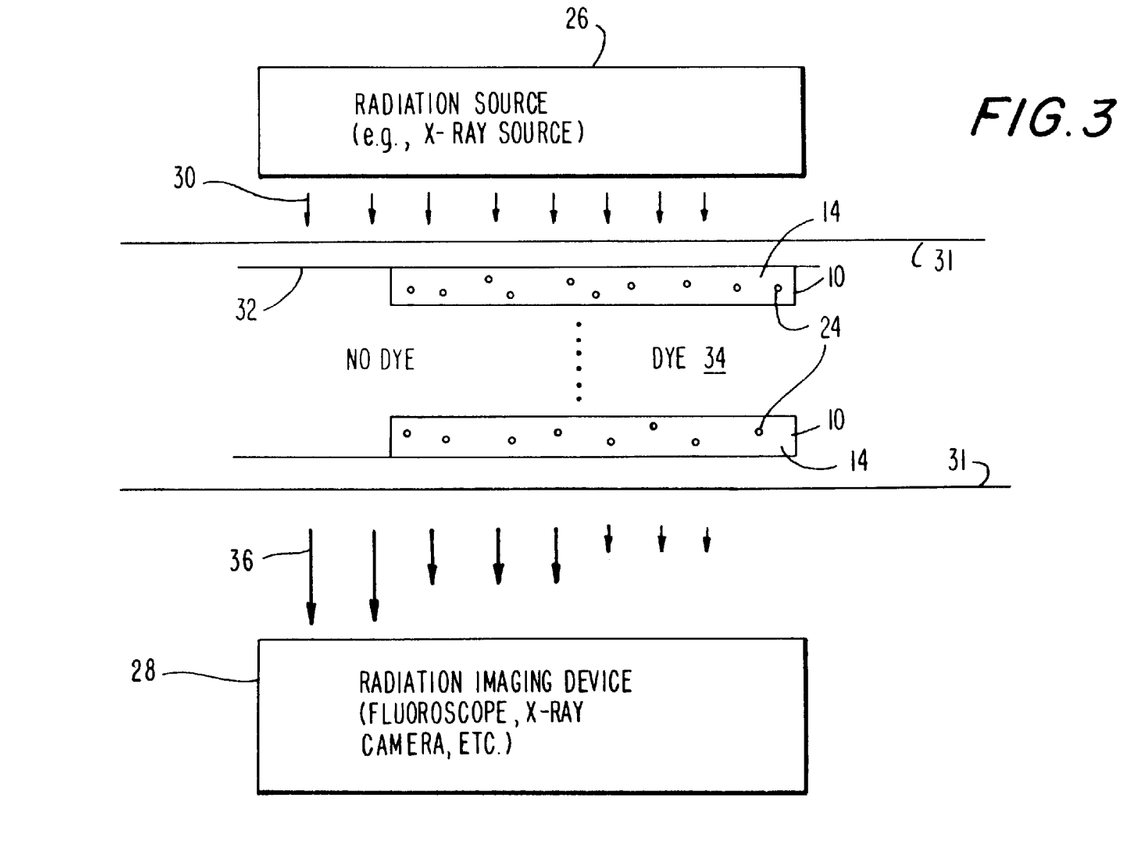
FIG. 3 is a schematic diagram showing fluoroscopic viewing of a flexible graft structure in accordance with the present invention.

In accordance with the present invention, graft structure 10 is radiopaque, so that graft structure 10 may be viewed during intraluminal installation procedures and during follow-up monitoring. As shown in FIG. 3, graft 10 may be viewed using a radiation source 26 and a radiation imaging device 28. Radiation source 26 is preferably an x-ray source and radiation imaging device 28 is preferably a fluoroscope for imaging graft 10 in real time.

Graft structure 10 is preferably made radiopaque by providing a radiopaque substance such as radiopaque filler 24 in coating 14. Filler 24 is preferably provided fairly uniformly throughout a substantial portion (e.g., greater than about 50%) of coating 14 or throughout substantially the entire coating 14 so that a physician viewing graft structure 10 with a fluoroscope can readily ascertain the size and position of graft structure 10. The large discrete particles of filler 24 shown in FIG. 3 are for illustrative purposes only. Filler 24 is preferably a radiopaque compound containing fairly fine particles of barium, bismuth, tungsten, etc. The concentration of radiopaque filler to be used for a given radiopaque graft depends on the size of graft structure 10 and the radiopacity of the filler. A suitable filler concentration may be in the range of approximately 10–20 per cent. Graft structure 10 is preferably radiopaque enough to allow graft structure 10 to be fluoroscopically viewed, but is preferably not so radiopaque that graft structure 10 obscures the viewing of commonly-used radiopaque dyes.

As shown in FIG. 3, incident radiation 30 from radiation source 26 passes through the patient's body 31 and body organ tubing 32, graft structure 10, and dye 34. The intensity of transmitted radiation 36 is greatest where neither graft structure 10 nor radiopaque dye 34 are present. Graft structure 10 reduces the intensity of transmitted radiation 36 sufficiently where graft structure 10 is present that graft structure 10 may be clearly viewed using radiation imaging device 28. Because graft structure 10 is fluoroscopically viewable, the physician can view the position of graft structure 10 during graft installation. In addition, during follow-up monitoring of an installed graft, the physician can assess the compliance (distensibility) of graft 10 by observing the behavior of graft 10 (e.g., as blood pulses through graft 10). Compliance monitoring over a period of days or weeks may allow the physician to asses whether there is ingrowth of natural tissue into the graft, because such tissue ingrowth typically reduces compliance. The physician can also assess the anastomosis of graft structures 10 to body organ tubing 16 and can detect the presence of holes, kink failures, bursts, etc. The physician can view the position of graft structure 10 during graft installation and can visually monitor graft structure 10 during follow-up monitoring without introducing a radiopaque dye into the patient.

Sometimes the physician may desire to introduce radiopaque dye into the patient's body organ tubing. For example, the physician may want to ascertain whether blood is flowing properly through the patient's vascular system in the vicinity of a vascular surgery site. The use of radiopaque dyes to visualize the patient's vascular system is well known and many physicians rely upon this technique, particularly during surgery and during the first 48 hours after surgery, before the patient has been discharged from the hospital.

The radiopacity of graft structure 10 is sufficiently low that graft structure 10 does not obscure standard radiopaque dyes when such dyes flow through graft structure 10. As schematically illustrated in FIG. 3, the intensity of transmitted radiation 36 through the portion of graft structure 10 that contains radiopaque dye 34 is substantially less than the intensity of transmitted radiation 36 through the portion of graft structure 10 that does not contain radiopaque dye 34. This allows physicians to use standard radiopaque dye diagnostic procedures to detect, e.g., the formation of blood clots in and around graft structure 10. The ability to view the flow of dye 34 through graft structure 10 is therefore an important attribute of graft structure 10 that may be used during follow-up monitoring of the patient.

Figure 4:
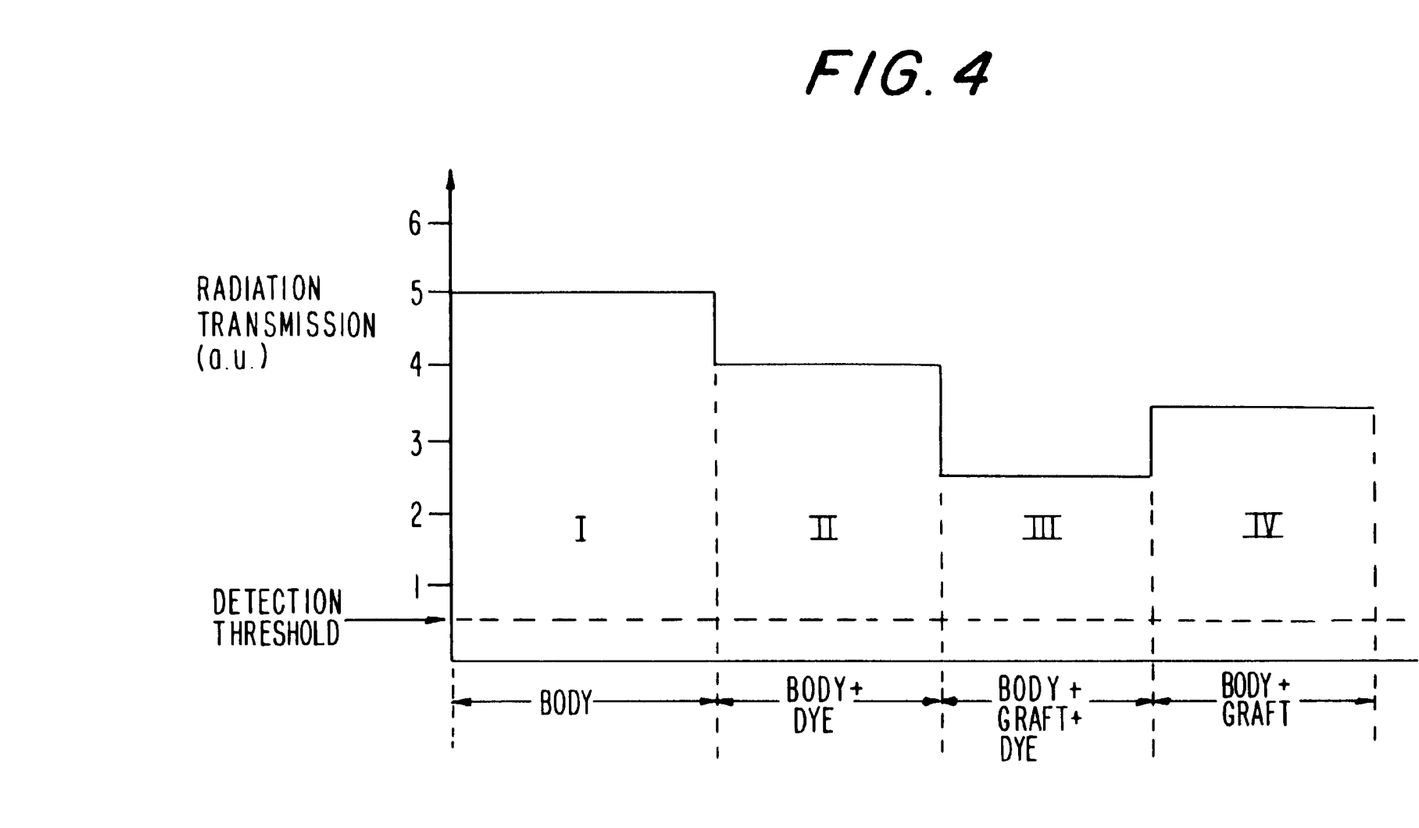
FIG. 4 is a schematic diagram comparing radiation transmission levels through various structures in accordance with the present invention.

The transmission of radiation through various structures is shown in FIG. 4 (in arbitrary units). Area I shows a level of radiation transmission (i.e., 5 a.u.) for a typical patient's body (including body organ tubing). Area II shows how transmission is reduced (i.e., to 4 a.u.) in those regions of the patient in which incident radiation passes through both the body and a region (i.e., body organ tubing of average size) containing dye 34 (FIG. 3). This allows the physician to view the flow of radiopaque dye through the patient's body. Area III shows that the level of radiation transmission is reduced further (i.e., to 2.5 a.u.) when incident radiation passes through graft structure 10 in addition to the body and radiopaque dye regions of area II. In area IV, transmission is greater than in area III, because incident radiation only passes through the patient's body and graft structure 10.

If the total level of transmitted radiation in any region falls below a given detection threshold (e.g., below 0.5 a.u. in the example of FIG. 4), then radiation imaging device 28 will not be able to discriminate pattern or structure within that region. The ability to view the flow of radiopaque dye through graft structure 10 therefore depends upon the transmitted radiation level of area IV being above this threshold level. With the arrangement shown in FIG. 4, the level of radiation transmission through body and graft regions (area IV) is significantly greater than the level of transmission through body, graft, and dye regions (area III) and the radiation transmission level in body and graft regions (area IV) is well above the detection threshold limit. Dye 34 passing through graft structure 10 is therefore not obscured (i.e., lowered below the detection threshold) by the radiopacity of graft structure 10.

Figure 5:
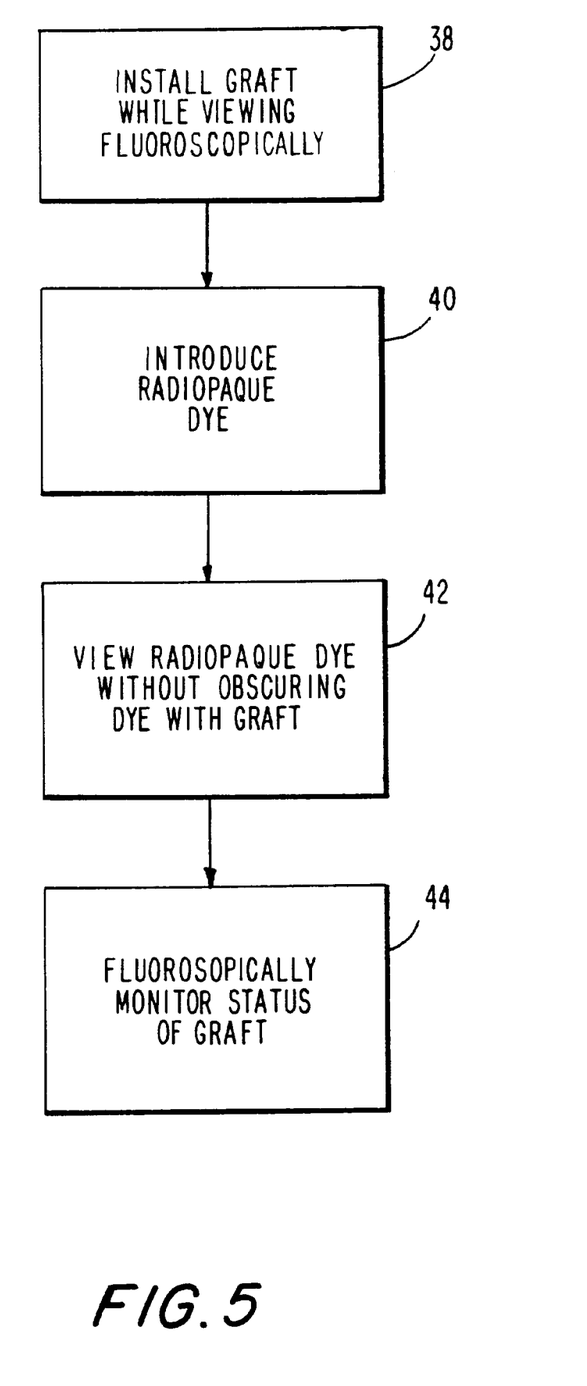
FIG. 5 is a flow chart showing steps involved in the process of installing and viewing a flexible graft structure in accordance with the present invention.

Steps involved in using graft structures 10 are shown in FIG. 5. At step 38, the physician installs graft structure 10 into the patient's body. Graft installation may be surgical or may involve intraluminal delivery (e.g., delivery through the patient's vascular system). During step 38, the physician may view graft structure 10 with a radiation imaging device such as a fluoroscope. Viewing graft structure 10 in real time during installation of graft structure 10 aids proper placement of graft structure 10 by the physician.

At step 40, the physician may introduce a standard radiopaque dye into the patient's body organ tubing (e.g., by injecting the dye into the patient's vascular system). The radiopaque dye may be fluoroscopically viewed at step 42. The flow of radiopaque dye may be viewed inside graft structure 10 without obscuring the dye with graft structure 10. In vascular applications, this allows the physician to observe whether blood clots have formed in graft structure 10.

Regardless of whether radiopaque dye has been introduced into the patient, the physician can fluoroscopically monitor the status of the installed graft structure 10 during a follow-up procedure at step 44. Fluoroscopic follow-up monitoring is possible due to the radiopacity of graft structure 10. Follow-up monitoring may involve fluoroscopically observing the distensibility of graft structure 10 and fluoroscopically monitoring graft structure 10 for leaks, kink failures, bursts, aneurysms, etc. Follow-up monitoring may also involve fluoroscopically assessing the anastomosis of graft structure 10 to the patient's body organ tubing.

It will be understood that the foregoing is only illustrative of the principles of the invention, and that various modifications can be made by those skilled in the art without departing from the scope and spirit of the invention.

What is claimed is:

1. A fluoroscopically-visible flexible graft structure for installation in the body of a patient, comprising:

a flexible elastic tubular structure having a frame and an elastic fluid-retaining coating that covers the frame; and a radiopaque substance distributed throughout a substantial portion of the coating so that the elastic tubular structure is fluoroscopically visible when the graft is inside the body of the patient.

2. The graft structure defined in claim 1 wherein the frame comprises a metal mesh frame for supporting the elastic tubular structure.

3. The graft structure defined in claim 2 wherein the metal mesh frame further comprises a nitinol mesh frame.

4. The graft structure defined in claim 2 wherein the coating comprises an elastic coating on the metal mesh frame.

5. The graft structure defined in claim 2 wherein the coating comprises a silicone coating on the metal mesh frame.

6. The graft structure defined in claim 1 wherein radiopaque dye is introduced into the elastic tubular structure, the graft structure further comprising a quantity of the radiopaque substance that allows the graft structure to be fluoroscopically viewed without obscuring the radiopaque dye.

7. The graft structure defined in claim 1 wherein the radiopaque substance comprises a radiopaque filler compound containing a metal selected from the group consisting of: barium, bismuth, and tungsten.

8. The graft structure defined in claim 1 wherein the radiopaque substance is distributed substantially throughout the entire coating.

9. A method for using a fluoroscopically-visible flexible graft structure inside the body of a patient, comprising the steps of:

installing a flexible graft structure in the body of the patient that has a flexible elastic tubular structure having a frame and an elastic fluid-retaining coating that covers the frame with a radiopaque substance distributed throughout a substantial portion of the coating; and fluoroscopically viewing the flexible graft structure when the flexible graft structure is inside in the body of the patient.

10. The method defined in claim 9 wherein the step of installing the flexible graft structure having a frame and an elastic fluid-retaining coating that covers the frame further comprises the step of installing a flexible graft structure having a metal mesh frame that supports the elastic tubular structure.

11. The method defined in claim 10 wherein the step of installing the flexible graft structure having the metal mesh frame further comprises the step of installing a flexible graft structure having a nitinol mesh frame that supports the elastic tubular structure.

12. The method defined in claim 10 wherein the step of installing the flexible graft structure having the metal mesh frame further comprises the step of installing a flexible graft structure having an elastic tubular structure with an elastic coating formed on the metal mesh frame.

13. The method defined in claim 10 wherein the step of installing the flexible graft structure having the metal mesh frame further comprises the step of installing a flexible graft structure having an elastic tubular structure with a silicone coating formed on the metal mesh frame.

14. The method defined in claim 9 further comprising the steps of:

introducing radiopaque dye into the flexible graft structure; and fluoroscopically viewing the radiopaque dye within the flexible graft structure without obscuring the radiopaque dye with the graft structure.

15. The method defined in claim 9 wherein the step of installing the flexible graft structure further comprises the step of installing a flexible graft structure having a radiopaque filler compound containing a metal selected from the group consisting of: barium, bismuth, and tungsten.

16. The method defined in claim 9 wherein the step of installing the flexible graft structure that has a flexible elastic tubular graft structure having a frame and an elastic fluid-retaining coating that covers the frame further comprises the step of installing a flexible graft structure having an elastic tubular structure in which the radiopaque substance is distributed substantially throughout the entire coating.

* * * * *

UNITED STATES PATENT AND TRADEMARK OFFICE
CERTIFICATE OF CORRECTION

PATENT NO.   : 6,048,362
DATED        : April 11, 2000
INVENTOR(S)  : Todd Allen Berg It is certified that error appears in the above-identified patent and that said Letters Patent is hereby corrected as shown below:

Title page,
UNITED STATE PATENT DOCUMENTS, change "5,628,788 5/1997 Pinchuk et al." to -- 5,628,788 5/1997 Pinchuk --.

Column 6,
Line 38, change "inside in the body" to -- inside the body --.

Signed and Sealed this

Twenty-second Day of January, 2002

Attest:

JAMES E. ROGAN
*Attesting Officer*   *Director of the United States Patent and Trademark Office*